United States Patent [19]

Pawloski et al.

[11] Patent Number: 5,032,301

[45] Date of Patent: Jul. 16, 1991

[54] HIGH PERFORMANCE LUBRICANTS COMPRISING TRIAZINE DERIVATIVES

[75] Inventors: Chester E. Pawloski, Bay City; Joseph E. Dunbar; Muthiah N. Inbasekaran, both of Midland, all of Mich.

[73] Assignee: The Dow Chemical Company, Midland, Mich.

[21] Appl. No.: 505,820

[22] Filed: Apr. 6, 1990

[51] Int. Cl.$^5$ ................ C10M 105/08; C10M 105/56
[52] U.S. Cl. .............................................. 252/51.5 R
[58] Field of Search ........................... 252/51.5 R, 51; 544/215

[56] References Cited

U.S. PATENT DOCUMENTS

| | | | |
|---|---|---|---|
| 3,038,900 | 6/1962 | Dess | 252/51.5 R |
| 3,113,943 | 12/1963 | Johns et al. | 252/51.5 R |
| 3,313,731 | 4/1967 | Dolle, Jr. et al. | 252/51.5 R |
| 3,408,411 | 10/1968 | McLoughlin et al. | 260/646 |
| 3,518,195 | 6/1970 | Garth | 252/51.5 |
| 3,523,118 | 8/1970 | Emerson et al. | 260/248 |
| 3,654,273 | 4/1972 | Schuman et al. | 252/51.5 R |
| 3,708,483 | 1/1973 | Anderson et al. | 260/248 CS |
| 3,734,976 | 5/1973 | Dorfman et al. | 260/823 |
| 3,816,416 | 6/1974 | Croft et al. | 260/248 CS |
| 3,845,051 | 10/1974 | Zollinger et al. | 260/248 CS |
| 4,324,673 | 4/1982 | Christian et al. | 252/51.5 R |
| 4,472,290 | 9/1984 | Caporiccio et al. | 252/51.5 R |

FOREIGN PATENT DOCUMENTS 50-117727 9/1975 Japan .

OTHER PUBLICATIONS

Chemical Abstracts 52126n.
Chemical Abstracts 70845e.
Nobuoishikawa and Hiro-o Harada, "The Prepration of 1-Aryloxy- and 1,1-Bis(aryloxy)Polyfuoroolefins from Hexafluoropropene and Octafluoroisobutylene," *Nippon Kaoaku Kai-shi*, 2 (1975), pp. 311, 315.
Hiro-O Harada and Nobuo Ishikawa, "Electronic Effect of Aryl Groups on the Z/E Ratio of 1-Aryloxypentafluoropropenes," *Journal of Fluorine Chemistry*, 11 (1978), pp. 87–92.
Robert L. Dressler and John A. Young, "Fluorocarbon Nitrogen Compounds, XII, Catalytic Perfluoroalkylation of Halotriazines," *Journal of Organic Chemistry*, 32 (1967), pp. 2004–2005.
R. D. Chambers, J. A. Jackson, W. K. R. Musgrave and R. A. Storey, "Reactions Involving Fluorideion, Part I. The Polyfluoroalkylation of Fluorinated Aromatic Systems," *J. Chem. Soc.*, (C) (1968), pp. 2221–2227.

Primary Examiner—Margaret B. Medley

[57] ABSTRACT

Triazines substituted with at least one aryloxy perfluoroisopropyl moiety are disclosed. These compounds, either alone or as additives, are useful as high temperature lubricants.

13 Claims, No Drawings

HIGH PERFORMANCE LUBRICANTS COMPRISING TRIAZINE DERIVATIVES

BACKGROUND OF THE INVENTION

The present invention is related to substituted triazines.

Various triazine compounds are known and have been widely used as herbicides. Some existing triazine compounds are also taught to be useful as high temperature or high performance lubricants. For example, U.S. Pat. No. 3,845,051 teaches the utility of certain $\alpha,\omega$-di-s-triazinyl n-perfluoropolyoxaalkanes as hydraulic fluids and lubricants capable of withstanding the increasing thermal and oxidative stress conditions of newer aerospace systems. U.S. Pat. No. 3,816,416 teaches that $\alpha,\omega$-di-s-triazinyl n-perfluorooxaalkanes are useful in similar applications. U.S. Pat. No. 3,518,195 teaches that a guanamine substituted with a perfluoropolypropoxy polymer is useful to stabilize perfluorinated polyether oils.

The demands placed on these materials and other existing lubricants continue to undergo significant changes. Engines are being developed for automotive and aeronautic applications that have requirements dramatically different from those of engines currently in use. It is anticipated that these engines will operate at temperatures exceeding 250° C. and will be constructed using materials new or different from those currently in use. Thus, what is needed are novel compounds useful as lubricants or lubricant additives that are stable at the high use temperatures while possessing the other properties required of lubricants.

SUMMARY OF THE INVENTION

The present invention is directed to triazines substituted with at least one aryloxy perfluoroisopropyl moiety. The triazine may be fully substituted with the aryloxy perfluoroisopropyl moieties or may have additional substituents selected from the group consisting of fluoro and aryloxy or substituted aryloxy.

The compounds and compositions of the present invention may be useful as lubricants and herbicides.

DETAILED DESCRIPTION OF THE ILLUSTRATIVE EMBODIMENTS

The triazines of the present invention preferably correspond to the formula:

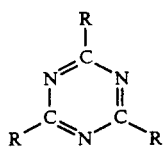

(I)

wherein R is independently in each occurrence fluorine, A or B wherein A is represented by the formula

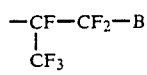

(II)

and B is represented by the formula

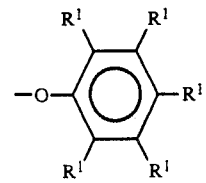

(III)

wherein $R^1$ is separately in each occurrence hydrogen, trifluoromethyl, phenyl, bromo, chloro, fluoro, nitro, cyano,

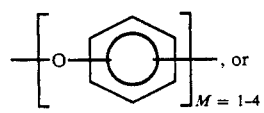

(IV)

or

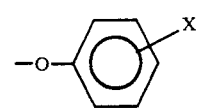

(V)

wherein X is fluoro, trifluoromethyl or $-O(CF_2)_pF$ wherein p is from one to about three, preferably three, with the proviso that at least one substituent on the triazine is A.

The compounds of the present invention are preferably prepared in a multi-step process in which an aryloxide is reacted with perfluoropropene to form a perfluoropropenylaryloxy derivative. This derivative is in turn reacted with a perhalotriazine to produce the novel substituted triazines of this invention.

Various methods are known by which phenols or other aryl compounds including thiophenols may be reacted with an alkali metal such as sodium to form a phenoxide or aryloxide which in turn reacts with hexafluoropropene. Examples of methods of prepare the substituted hexafluoropropenes are found in *Nippon Kaoaku Kai-shi*, 1975, No. 2, 311–315; Japanese Patent Disclosure Kokai 50-117727; and U.S. Pat. No. 3,180,895, hereby incorporated by reference.

In a preferred embodiment, the selected phenol is reacted with sodium or potassium in a solvent such as glyme, and the resulting aryloxide is reacted with hexafluoropropene at about $-40°$ C. The resulting aryloxy substituted perfluoropropene is then purified by distillation. If desired, the aryloxy substituted perfluoropropene may be reacted with a second aryloxide which may be the same or different from the first to form a di-aryloxy substituted perfluoropropene.

The perfluoropropene derivatives prepared in this way correspond to the following formula:

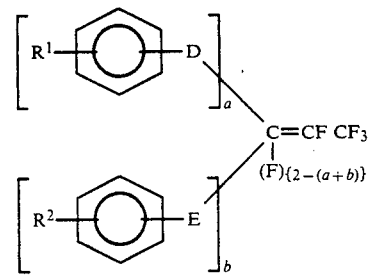

(VI)

wherein R[1] is as defined above; R[2] is phenyl, trifluoromethylphenoxy, trifluoromethyl, or

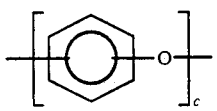
(VII)

wherein c is from one to about four; D is oxygen; E is oxygen or sulfur; a is 1 or 2; and b is 0 or 1 with the proviso that the sum of a and b is 1 or 2. In a preferred embodiment, b is zero and a is one.

In addition to being useful as intermediates in the preparation of the substituted triazines of this invention, these perfluoropropene derivatives are useful as lubricants and herbicides.

Non-limiting examples of preferred perfluoropropene derivatives include 1-phenoxy-1,2,2,3,3-pentafluoropropene; 1-phenoxy-1-(3-phenoxy-3-phenoxyphenoxy)-2,2,3,3-tetrafluoropropene; 1-phenylthio-1-(3-phenoxyphenoxy)-2,3,3,3-tetrafluoropropene; 1-(3-trifluoromethylphenoxyphenoxy)-1,2,3,3,3-pentafluoropropene; 1,1-bis(3-phenoxyphenoxy)-2,3,3,3-tetrafluoropropene; and 1-(3-phenoxyphenoxy)-1,2,3,3,3-pentafluoropropene.

The perfluoropropene derivatives prepared in the first step are then reacted with perhalogenated, preferably perfluorinated, triazines using known methods to produce the novel aryloxy perfluoroisopropyl substituted triazines of the present invention. Such processes are described in, for example, *J. Chem. Soc.* (C), 2221-2227 (1968) and *J. Org. Chem.* 32, 2004-2005 (1967), hereby incorporated by reference.

The compounds of this invention are useful as lubricants over extended temperature ranges. They may be used alone and also may be used in conjunction with various additives to improve their performance. Additionally, they may themselves be used as additives with other base stocks.

When used as an additive to a base stock, the triazines of the present invention must be compatible with the base stock. By compatible, it is meant that the triazines of the present invention may be readily dispersed or dissolved in the base stock, either with or without the addition of an appropriate surfactant. Examples of known lubricant bases useful in the compositions of this invention include organic oils and greases well known to those skilled in the art. When the triazines of the present invention are used as additives to conventional, compatible base stocks, it is preferred that the base stocks are polyglycols, polyphenyl ethers and polyol esters. It is more preferred that the base stocks are polyphenyl ethers such as 5P4E which is a polyphenyl ether having five phenyl groups and four ether linkages. Other preferred base stocks include polyol esters such as pentaerythritol tetra $C_{5-9}$ esters (PET).

The lubricant compositions of this invention comprise from about 0.1 to about 100 weight percent of the triazines of the invention. That is, the triazines of this invention may be used as a lubricant base stock (i.e., lubricant composition is up to about 100 weight percent triazine) or they may be used as additives with other lubricants (i.e., lubricant composition contains at least about 0.1 weight percent triazine).

When the triazines of this invention are used as lubricant additives, it is preferred that they are used in amounts of at least about 0.5 weight percent, more preferably at least about 5 weight percent. It is also preferred that the triazines of the present invention, when used as additives, are used in amounts of no greater than about 50 weight percent, preferably no greater than about 20 weight percent.

As discussed above, the triazines of the present invention may be used as lubricants themselves, either alone or with the addition of additives known in the art. When used as the lubricant base stock, additives useful in high temperature lubricants may be added. In this context, it is preferred that the triazine of this invention comprise at least about 50 weight percent, more preferably at least about 95 weight percent of the composition with one or more additives making up the remainder of the lubricant composition. Additionally, the triazines of this invention may be blended with other base stocks to prepare lubricants.

The following examples are provided for illustrative purposes only and should not be construed as limiting the invention in any way. Unless stated otherwise, all parts and percentages are by weight.

EXAMPLE 1

Preparation of 1,2,3,3,3-pentafluoro-1-(3-phenoxy-3-phenoxyphenoxy)propene

Five g (0.018 mole) of 3-phenoxy-3-phenoxyphenol, 100 ml of xylene and 1.2 g of KOH are placed into a flask equipped with a Dean-Stark trap. This mixture is stirred at reflux until water of reaction ceases to evolve. The mixture is cooled and 100 ml of tetrahydrofuran (THF) are added and the mixture is further cooled in a dry ice/acetone bath while 15 g of perfluoropropene are bubbled into the reaction mixture. The mixture is stirred for three hours while warming to room temperature. Next, 100 ml of water are added and the mixture is stirred. The product phase is separated, dried over sodium sulfate, filtered and distilled. The product propene is an oil obtained in a yield of 75 percent. The oil has a pour point below $-27°$ C., a boiling point of 150° C. at 1.0 mm Hg and a DSC of 373° C.

EXAMPLE 2

Preparation of 1-(3-phenoxyphenoxy)-1-(phenylthio)-2,3,3,3-tetrafluoropropene

Eleven g (0.1 mole) of thiophenol and 150 ml 1,2-dimethoxy ethane are placed into a flask and stirred under nitrogen while 2.3 g of metal sodium are added in portions. When this reaction is complete, 32 g of 1-(3-phenoxyphenoxy)perfluoropropene are added dropwise causing a slight exotherm. The mixture is stirred at 75° C. for six hours following this addition. After cooling, 150 ml of dilute base water solution is added and the mixture is stirred. The product layer is separated and washed with 150 ml water, separated, dried over sodium sulfate, filtered and distilled to produce the title compound as an oil in a yield of 38 percent. The oil has a pour point of $-26°$ C. and a boiling range of 150° to 190° C. at 0.5 mm Hg.

EXAMPLE 3

Preparation of 1,2,3,3,3-pentafluoro-1-propenyloxybenzene

Forty g (0.33) mole of sodium phenolate and 500 ml of THF are placed into a flask and stirred at dry ice/acetone bath temperature while 50 g of perfluoropropene is bubbled into the reaction mixture. The mixture is then stirred for four hours while warming to room temperature. The flask is then filled with cold water and stirred. This mixture is extracted with 300 ml of methylene chloride, separated and washed with 100 ml of salt solution. The product layer is separated, dried over sodium sulfate, filtered and distilled to produce a 52 percent yield of an oil with a boiling point range of 148°–154° C. The oil included about 90 percent of the product and about 10 percent of a hydrogen by-product.

EXAMPLE 4

Preparation of 2,4-difluoro-6-(1,1,2,3,3,3-hexafluoro-1-phenoxy-2-propyl)1,3,5-triazine One g (0.1 mole) of CsF and 22 g (0.1 mole) of 1-phenoxy perfluoropropene and 10 g (0.1 mole) of cyanuric fluoride are placed into a Parr bomb. The bomb is sealed and stirred at 100°–130° C. for 16 hours. After cooling, the solids are filtered off and 30 g of oil are obtained. This is distilled to produce the product compound as an oil with a boiling point of 195° C. in a yield of 39 percent.

EXAMPLE 5

Preparation of (2,4-diphenoxy)-6-(1,1,2,3,3,3-hexafluoro-1-phenoxy-2-propyl)-1,3,5-triazine A 7 g portion of 2,4-difluoro-6-(1,1,2,3,3,3-hexafluoro-1-phenoxy-2-propyl)-1,3,5-triazine is placed into a flask with 100 ml of toluene and 15 g of 2,4,6-trimethylpyridine. This mixture is stirred at reflux for seven hours and then cooled. Next, 200 ml of dilute HCl water solution are added and the mixture is stirred. Solids are obtained and filtered off, rinsed with water and distilled at 250° C. at 0.5 mm Hg to produce 7 g of solids with a melting point of 234°–235° C. The identity of the product is confirmed by NMR spectra to be (2,4-diphenoxy)-6-(1,1,2,3,3,3-hexafluoro-1-phenoxy-2-propyl)-1,3,5-triazine. The product has a DSC of 385° C.

EXAMPLE 6

Preparation of 2,4,6-tris(1,1,2,3,3,3-hexafluoro-1-phenoxy-2-propyl)-1,3,5-triazine A 3.5 g portion of difluoro-6-(1-phenoxy-1,1,2,3,3,3-hexafluoro-2-propyl)-1,3,5-triazine, 11 g of perfluoropropenyloxy benzene and 3 g of CsF are placed into a Parr bomb. The bomb is sealed and the mixture is heated to 100° to 130° C. for 16 hours. The mixture is cooled and then filtered and distilled to produce 2,4,6-tris(1-phenoxy-1,1,2,3,3,3-hexafluoro-2-propyl)-1,3,5-triazine. The boiling point of the product is 220° C. at 0.1 mm Hg and its DSC is 374° C. The identity of the product is confirmed by NMR and mass spectra.

EXAMPLE 7

Preparation of 2,4,6-tris(1,1,2,3,3,3-hexafluoro-1-(3-phenoxyphenoxy)-2-propyl)-1,3,5-triazine A 10.8 g portion of cyanuric fluoride is added to 127.4 g of 1-(3-phenoxyphenoxy)-1,2,3,3,3-pentafluoropropene, 20 ml of tris(2-(2-methoxyethoxy)ethyl)amine, as a catalyst and 12 g of dry cesium fluoride in 200 ml dry ethylene glycol dimethyl ether under a nitrogen blanket. The mixture is heated with stirring at 64° C. to 69° C. for one hour and then heated under reflux at 88° C. for 43 hours and then cooled. The ethylene glycol dimethyl ether is removed by evaporation in vacuo to yield 159 g of a dark oil. The oil is stirred vigorously with 200 ml of water and then extracted with two 200 ml portions of ether. The combined ether extracts are washed successively with four 150 ml portions of water and then with one 200 ml portion of saturated aqueous sodium chloride solution. The ether phase is dried over $MgSO_4$ and the ether is removed by evaporation in vacuo to yield 124 g of a dark oil as crude product. The excess starting material is removed by distillation. The pot residue is flash chromatographed on silica gel using carbon tetrachloride as eluent. The solvent is removed by evaporation in vacuo and the residual oil is distilled to yield a pale yellow oil with a boiling point of 255°–258° C. at 0.01 mm Hg. Analytical analysis shows carbon, 53.13; hydrogen, 2.48; nitrogen, 3.83; and fluorine, 31.56 which is consistent with 2,4,6-tris(1,1,2,3,3,3-hexafluoro-1-(3-phenoxyphenoxy)-2-propyl)-1,3,5-triazine.

EXAMPLE 8

2,4,6-Tris(1,1,1,2,3,3-hexafluoro-(3-phenoxy)-2-propyl)-1,3,5-triazine

To a stirred solution of 5.50 g of phenyl pentafluoroallyl ether, 1.30 g of cesium fluoride and a catalytic amount of 18-crown-6 in 25 ml of ethylene glycol dimethyl ether under a blanket of nitrogen is added 0.6 ml of cyanuric fluoride. The stirred reaction mixture is heated at reflux for 24 hours, after which the solvent is removed by evaporation in vacuo, leaving the crude product as 6.1 g of amber oil. The oil is dissolved in 75 ml of ethyl ether, and the ether solution is washed successively with three 25 ml portions of water and, finally, with one 25 ml portion of saturated aqueous sodium chloride solution. The ether solution is dried over anhydrous magnesium sulfate, after which the magnesium sulfate is removed by filtration, and the ether is removed by evaporation in vacuo, leaving 4.8 g of amber oil. The oil is flash chromatographed on silica gel with methylene chloride as eluent to give 1.6 g of the product as a light yellow oil shown to be pure by high pressure liquid chromatography. Identity of the product is confirmed by mass spectroscopy.

EXAMPLE 9

Friction and wear test

The anti-wear and extreme pressure characteristics of the compounds of this invention are measured using the four-ball test using a Falex friction and wear tester. In this example, the compound tested is 2,4,6-tris(1,1,2,3,3,3-hexafluoro-1-(3-phenoxy-phenoxy)-2-propyl)-1,3,5-triazine. The four-ball bearing balls used in this test are made of M50 steel. Test load is 67 Newtons (33.1 pounds). The test speed is 1200 rpm and each test is run for one hour unless noted otherwise. About 60 cubic centimeters of fluid are used for each test. Each test is conducted at 200° C. During each test, the torque as a function of the wear cycles is monitored on a real time data acquisition basis for data analysis to yield the coefficient of friction. Optical microscope pictures of the bearing balls are taken at the test completion and scar diameter is measured from these pictures. At the conclusion of the test, the wear scar diameter is 0.43 mm and the coefficient of friction is 0.102 demonstrating the effectiveness of the compound as a lubricant.

What is claimed is:

1. A triazine compound which corresponds to the formula

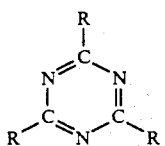

wherein R is independently in each occurrence fluorine, A or B wherein A is represented by the formula

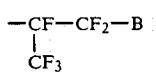

and B is represented by the formula

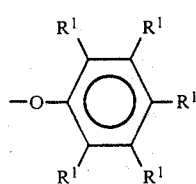

wherein $R^1$ is separately in each occurrence hydrogen, trifluoromethyl, phenyl, bromo, chloro, fluoro, nitro, cyano,

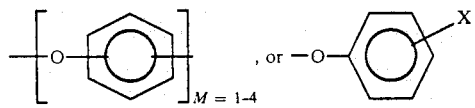

wherein X is fluoro, trifluoromethyl or $-O(CF_2)_pF$ wherein p is from one to about three with the proviso that at least one substituent on the triazine is A.

2. The compound of claim 1 wherein the triazine is fully substituted by A.

3. The compound of claim 2 which is 2,4,6-tris(1,1,2,3,3,3-hexafluoro-3-phenoxy-2-propyl)-1,3,5-triazine.

4. The compound of claim 2 which is 2,4,6-tris(1,1,2,3,3,3-hexafluoro-1-(3-phenoxyphenoxy)-2-propyl)-1,3,5-triazine.

5. The compound of claim 2 which is 2,4,6-tris(1,1,2,3,3,3-hexafluoro-1-(4-phenoxyphenoxy)-2-propyl)-1,3,5-triazine.

6. The compound of claim 1 wherein p is 3, R is in two occurrences fluorine and is in one occurrence A.

7. The compound of claim 6 which is 2,4-difluoro-6-(1,1,2,3,3,3-hexafluoro-1-phenoxy-2-propyl)-1,3,5-triazine.

8. The compound of claim 1 wherein p is 3, R is in one occurrence A and is in two occurrences B.

9. The compound of claim 8 which is (2,4-diphenoxy)-6-(1,1,2,3,3,3-hexafluoro-1-phenoxy-2-propyl)-1,3,5-triazine.

10. A lubricant composition comprising from at least about 0.1 weight percent to about 100 weight percent of at least one triazine which corresponds to the formula

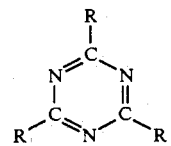

wherein R is independently in each occurrence A or B wherein A is represented by the formula

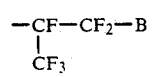

and B is represented by the formula

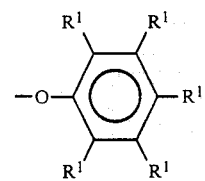

wherein $R^1$ is separately in each occurrence hydrogen, trifluoromethyl, phenyl, bromo, chloro, fluoro, nitro, cyano,

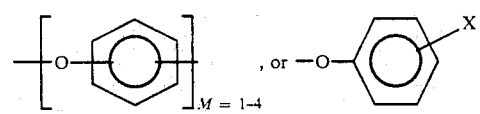

wherein X is fluoro, trifluoromethyl or $-O(CF_2)_pF$ wherein p is from one to about three and, optionally, a lubricant base stock and lubricant additives.

11. The composition of claim 10 wherein the triazine is selected from the group consisting essentially of 2,4,6-tris(1,1,2,3,3,3-hexafluoro-3-phenoxy-2-propyl)-1,3,5-triazine; (2,4-diphenoxy)-6-(1,1,2,3,3,3-hexafluoro-1-phenoxy-2-propyl)-1,3,5-triazine; 2,4,6-tris(1,1,2,3,3,3-hexafluoro-1-(3-phenoxyphenoxy)-2-propyl)-1,3,5-triazine; and 2,4,6-tris(1-(4-phenoxyphenoxy)-1,1,2,3,3,3-hexafluoro-2-propyl)-1,3,5-triazine.

12. A lubricant composition comprising from at least about 0.1 weight percent to about 100 weight percent of at least one triazine substituted with at least one phenoxy substituted perfluoroisopropyl moiety and, optionally, a lubricant base stock and lubricant additives.

13. The composition of claim 11 wherein the triazine is 2,4,6-tris(1,1,2,3,3,3-hexafluoro-3-phenoxy-2-propyl)-1,3,5-triazine.

* * * * *